United States Patent [19]
DeVincentis et al.

[11] Patent Number: 5,391,367
[45] Date of Patent: Feb. 21, 1995

[54] ANTIFUNGAL NAIL SOLUTION

[75] Inventors: Teresa J. DeVincentis, Flanders; Darius D. Dubash, Pine Brook; Debbie L. Burnett, Basking Ridge; Athanasios S. Ladas, Parsippany, all of N.J.

[73] Assignee: Pfizer Inc., New York, N.Y.

[21] Appl. No.: 97,422

[22] Filed: Jul. 28, 1993

[51] Int. Cl.⁶ .................................................. A61K 7/04
[52] U.S. Cl. .............................. 424/61; 514/397; 514/777
[58] Field of Search ................ 424/61; 514/397, 777

[56] References Cited

U.S. PATENT DOCUMENTS 3,914,131 10/1975 Hutchison ........................... 106/268
4,721,724 1/1988 Stettendorf et al. ................ 514/396

FOREIGN PATENT DOCUMENTS 0440298 8/1991 European Pat. Off. .
8702580 5/1987 WIPO .
8704617 8/1987 WIPO .

*Primary Examiner*—Gollamudi S. Kishore
*Assistant Examiner*—Jyothsna Venkat
*Attorney, Agent, or Firm*—Peter C. Richardson; Gregg C. Benson; Robert F. Sheyka

[57] ABSTRACT

A composition useful in the treatment of onychomycosis comprises tioconazole, a gel-forming agent and a hydro-alcoholic vehicle.

5 Claims, No Drawings

ANTIFUNGAL NAIL SOLUTION

BACKGROUND OF THE INVENTION

The present invention relates to a topical solution for fungal infections. More specifically, it relates to a topical solution for the treatment of fungal infections of the nails, or onychomycosis.

Onychomycosis, also called ringworm of nails, or tinea unguium, is a fungus infection of the nails causing thickening, roughness and splitting usually caused by *Trichophyton rubrum* or *Trichophyton mentagrophytes*.

European Patent Application No. 515312 refers to a topical formulation such as a nail varnish for treating onychomycosis comprising tertinafine and a polymeric film former such as polyvinylacetate or (meth)acrylic acid alkyl ester copolymerizates with quaternary ammonium groups or methylvinylethermaleic acid monoalkyl ester copolymerizates.

European Patent Application No. 440298 refers to a topical composition for the treatment of onychomycosis which comprises oxiconazole and a film-forming composition.

European Patent Application No. 292495 refers to a composition containing urea and propylene glycol and/or polyethylene glycol for the treatment of onychomycosis.

European Patent Application No. 247142 refers to a vehicle for applying drugs to human nails for the treatment of onychomycosis. The vehicle comprises from 2% to about 40% by weight of a hydrophilic, film-forming resin, and a pharmaceutically acceptable solvent for the resin. Upon drying, the vehicle is said to form a continuous self-supporting dry film. The vehicle has incorporated therein at least one antimycotic drug selected from the group consisting of sodium propionate, sodium pyrithone and cicloperox. U.S. Pat. No. 4,721,724 issued Jan. 26, 1988 refers to an antifungal composition containing clotrimazole, urea, a lipophilic wetting agent and a consistency imparting component.

SUMMARY OF THE INVENTION

In one embodiment, the present invention is directed to an antifungal composition comprising
 (a) an effective amount of tioconazole;
 (b) water;
 (c) an alcohol, and
 (d) a gel-forming agent, said composition when applied to the nails of a human infected with onychomycosis creating a reservoir from which tioconazole continuously penetrates the nail.

Preferred is the composition wherein the alcohol is ethanol.

Also preferred is the composition wherein said gel-forming agent is hydroxypropyl cellulose.

Further preferred is the composition further comprising the addition of a plasticizer with an especially preferred plasticizer being propylene glycol dipelargonate.

In another embodiment, the present invention is directed to an antifungal composition comprising
 (a) from about 15 to about 30 weight percent tioconazole;
 (b) from about 1 to about 10 weight percent water;
 (c) from about 50 to about 90 weight percent alcohol, and
 (d) from about 0.5 to about 5 weight percent of a gel-forming agent,
said composition when applied to the nails of a human infected with onychomycosis creating a reservoir from which tioconazole continuously penetrates the nails.

A preferred alcohol for use in the composition of the present invention is ethanol.

A preferred gel-forming agent for use in the composition of the present invention is hydroxypropyl cellulose.

Further preferred is the composition of the present invention which further comprises a plasticizer, preferably at from about 0.5 to about 10 weight percent, with an especially preferred plasticizer being propylene glycol dipelargonate.

In another embodiment, the present invention is also directed to a method for the treatment of onychomycosis comprising the application to the nails of a human in need of such treatment a composition of the present invention.

DETAILED DESCRIPTION OF THE INVENTION

1-{2,4-dichloro-$\beta$-[(2-chloro-3-thenyl)-oxy]phenethyl}imidazole or tioconazole, its synthesis and formulation into a number of dosage forms, including creams, is described in U.S. Pat. No. 4,062,966 issued Dec. 13, 1977, the disclosure of this patent being incorporated herein by reference.

It has now been found by in vitro microbiological tests that a topical tioconazole formulation is effective in the treatment of onychomycosis. The present formulation contains a hydro-alcoholic vehicle in conjunction with a hydrophilic gel-forming agent. It has been shown that this aqueous vehicle delivers about twice the quantity of tioconazole to the nail, as opposed to an organic based formulation.

The present formulation also provides other advantages over organic based vehicles which tend to dehydrate the nail. The use of a hydro-alcoholic vehicle in combination with the hydrophilic gel forming agent aids in maintaining a higher state of hydration. As a result of this higher state of hydration, flux studies have shown that there is a shorter lag period and a reservoir effect is created from which tioconazole continuously penetrates the nail. While not wishing to be bound by theory, it is believed this reservoir effect has a positive impact on the product's therapeutic efficacy.

The amount of tioconazole in the formulation can range from about 15 to about 30 weight percent. Preferably, the amount of tioconazole is about 20 weight percent.

The amount of water in the formulation can range from about 1 to about 10 weight percent. Preferably, the amount of water is about 4 weight percent.

Since the formulation of the present invention uses a hydro-alcoholic vehicle, the alcohol used in the formulation should be substantially water-free. Preferably, a 200 proof (100%) alcohol is used. An especially preferred alcohol is ethanol. If ethanol is used, the amount in the formulation can range from about 50 to about 90 weight percent, preferably about 70 weight percent.

The hydrophilic gel forming agent which is used in the formulation of the present invention may be any water-soluble resin derived from natural substances including cellulose, glucose, and sucrose. The preferred gel forming agent, hydroxypropyl cellulose (Klucel ®JF, Aqualon Co.), is a nonionic water-soluble propylene glycol ether of cellulose made by reacting alkali cellulose with propylene oxide at elevated temperatures and pressures. There are many viscosity grades available of hydroxypropyl cellulose which may be used in the formulations of the present invention. If hydroxypropyl cellulose is used, it is present in the formulation at from about 0.5 to about 5 weight percent, preferably at about 1.0 weight percent.

If desired, a plasticizer may also be added to the formulation of the present invention. The plasticizer aids in forming a continuous film when the formulation is applied to the nail. An especially preferred plasticizer is propylene glycol dipelargonate. If propylene glycol dipelargonate is used as the plasticizer, it is present at from about 0.5 to about 10 weight percent, preferably at about 5 weight percent.

Additionally, the formulation of the present invention may contain an emollient such as glycerin which, if present, is present at a concentration of from about 0.5 to about 5 weight percent, preferably at about 1.0 weight percent.

The formulation of the present invention may be packaged in a number of containers. It may be supplied in a bottle with a brush applicator similar to a nail polish. It may also be supplied in an applicator tipped bottle. It may also be supplied in a glass rod applicator bottle.

Having described the invention in general terms, reference is now made to specific examples. It is to be understood that these examples are not meant to limit the present invention, the scope of which is determined by the appended claims.

EXAMPLE 1

TIOCONAZOLE 20% w/w, NAIL SOLUTION
(Tioconazole 20%)

| Ingredient | Grade | Manufacturer | % w/w | Weight (GM) |
|---|---|---|---|---|
| Alcohol SDA 40,200 Proof 1 | — | Union Carbide Corporation | 69.0 | 44850.0 |
| Tioconazole | USP | Pfizer Limited | 20.0 | 13000.0 |
| Glycerin | USP | Procter & Gamble | 1.0 | 650.0 |
| Purified Water | USP | Pfizer, Inc. | 4.0 | 2600.0 |
| Propylene Glycol Dipelargonate 2 | — | Henkel Corp.- Emery Group | 5.0 | 3250.0 |
| Hydroxypropyl Cellulose 3 | NF | Aqualon Company | 1.0 | 650.0 |
| TOTAL | | | 100.0 | 65000.0 |

1. Ethanol 200 PF SY SDA-40-2
2. Emerest ® 2388
3. Klucel ® JF

In a pre-sanitized, suitable sized stainless steel tank was introduced 44850.0 grams of alcohol SDA 40,200 Proof. To this was slowly added and dissolved 13000.0 grams of tioconazole with the aid of an air-driven Lightnin Mixer. The solution was mixed for approximately twenty-five minutes to solubilize the tioconazole. To the alcoholic solution from the previous steps was added 650.0 grams of glycerin, 2600.0 grams of purified water, and 3250.0 grams of propylene glycol dipelargonate with constant agitation provided by a Lightnin Mixer.

The final step was to add and completely hydrate with constant agitation 650.0 grams of hydroxypropyl cellulose and mix for approximately one and one half hours. The entire batch was filtered through a pre-sanitized, in-line stainless steel filtering unit fitted with #100 mesh screen; and the filtrate was collected in a pre-sanitized, tared holding tank.

Each 5 ml bottle was filled with approximately 4.48 grams of filtered solution to within ±2% of the intended fill weight using a suitable liquid filling machine. 10 ml bottles were also filled. Each bottle was capped and torqued at approximately 8 -16 inch-lb, and inspected for fill abnormalities.

We claim:
1. A topical antifungal composition comprising:
   (a) from about 15 to about 30 weight percent tioconazole;
   (b) from about 1 to about 10 weight percent water;
   (c) from about 50 to about 90 weight percent alcohol;
   (d) from about 0.5 to about 5 weight percent of a water-soluble gel-forming agent which is hydroxy propyl cellulose and
   (e) from about 0.5 to about 10 weight percent of propylene glycol dipelargonate as the plasticizer, said composition when applied to the nails of a human infected with onychomycosis creating a reservoir from which tioconazole continuously penetrates the nail.

2. A composition according to claim 1 wherein said alcohol is ethanol.

3. A composition according to claim 1 further comprising the addition of glycerin.

4. A composition according to claim 3 wherein glycerin is present at a concentration of from about 0.5 to about 5.0 weight percent.

5. A method for the treatment of onychomycosis comprising the application to the nails of a human in need of such treatment an effective amount of the composition of claim 1.

* * * * *